United States Patent [19]

Benner et al.

[11] 4,224,247

[45] Sep. 23, 1980

[54] RECOVERY OF PARA-AMINOPHENOL

[75] Inventors: Roland G. Benner, New Providence, N.J.; Paul D. Henson, Roanoke, Va.

[73] Assignee: Mallinckrodt, Inc., St. Louis, Mo.

[21] Appl. No.: 958,868

[22] Filed: Nov. 8, 1978

[51] Int. Cl.$^2$ ............................................. C07C 91/44
[52] U.S. Cl. ................................. 260/575; 260/576
[58] Field of Search ............................... 260/575, 576

[56] References Cited

U.S. PATENT DOCUMENTS

| | | | |
|---|---|---|---|
| 2,048,823 | 7/1936 | Semon | 260/809 |
| 2,053,785 | 9/1936 | Semon | 260/809 |
| 2,087,199 | 7/1937 | Clifford | 260/809 |
| 3,383,416 | 5/1968 | Benner | 260/575 |
| 3,418,373 | 12/1968 | Summers et al. | 260/576 |
| 3,432,460 | 3/1969 | Spacht . | |
| 3,717,680 | 2/1973 | Baron et al. | 260/575 |

*Primary Examiner*—Winston A. Douglas
*Assistant Examiner*—J. V. Howard

*Attorney, Agent, or Firm*—Lawrence Rosen; E. Janet Berry

[57] ABSTRACT

An improved method for the recovery of para-aminophenol from crude solutions thereof such as obtained by the catalytic hydrogenation of nitrobenzene in an aqueous acid reaction medium. The method comprises neutralizing the cold, acidic solution containing the crude para-aminophenol whereby a very fine fluffy para-aminophenol precipitates. When an aromatic amine selected from the group consisting of aniline, mixed toluidines, ortho-toluidine, mixed xylidines, and mixtures thereof is admixed therewith an upper layer containing the para-aminophenol suspended in the aromatic amine forms when allowed to settle. A clear lower layer containing about 70 to 90% of the ammonium sulfate solution is separated and discarded. The upper layer which contains the aromatic amine and the para-aminophenol can be used as a source of para-aminophenol for producing para-aminophenol derivatives such as diaryl para-phenylenediamines.

12 Claims, No Drawings

RECOVERY OF PARA-AMINOPHENOL

The present invention relates to an improved method for the recovery of para-aminophenol. More particularly, the invention pertains to a process wherein para-aminophenol is recovered from a crude acidic solution thereof by neutralizing it in the cold state and then contacting it with an aromatic amine. The para-aminophenol floats in the aromatic amine upper layer, which is separated from the clear lower aqueous layer.

A recently developed, and probably one of the most economical processes, for making para-aminophenol involves the catalytic reduction of nitrobenzene with hydrogen in a dilute sulfuric acid solution in accordance with the teachings of U.S. Pat. No. 3,383,416 (Benner). Although the para-aminophenol obtained by this procedure is suitable for most uses, it contains small quantities of impurities which make it unsuitable for producing a pharmaceutical grade derivatives such as N-acetyl-p-aminophenol (acetaminophen). Accordingly, a purification step as described in U.S. Pat. No. 3,717,680 (Baron and Benner) is included in the processing of the reaction mixture. This purification step involves the addition of an aromatic amine such as aniline in sufficient quantities to dissolve the impurities such as 4,4'-diaminoether but in insufficient quantities to dissolve appreciable quantities of para-aminophenol at temperatures of 15° to 40° C. at which the para-aminophenol crystals are filtered from the mother liquor. The aniline containing the impurities filters with the mother liquor.

After removal of catalyst and unreacted nitrobenzene, the reaction mass consists of an aqueous solution containing up to about 12% para-aminophenol, up to about 4% aniline, up to about 18% sulfuric acid, and impurities. In order to isolate the para-aminophenol in a purified form, the solution is neutralized with ammonia and about one part of aniline is added for each part of para-aminophenol. The solution is then cooled to below 30° C. The resulting crystals of para-aminophenol are filtered from the aqueous ammonium sulfate solution and the aniline containing the impurities. The crystals are washed with aniline, then toluene and finally with dilute sodium bisulfite solution and then dried in a vacuum drier. The upper layer of aniline in the filtrate is separated from the lower layer of aqueous ammonium sulfate solution. The aniline is recovered by distillation. The ammonium sulfate solution can be used as a fertilizer after treatment to remove impurities which include small amounts of dissolved para-aminophenol.

Although the cost of nitrobenzene as a starting material for making para-aminophenol in accordance with the Benner Patent is relatively low, the cost of the finished para-aminophenol is relatively high because of the labor and equipment required in the many steps such as purification, crystallization, filtration, and drying involved in its manufacture. In addition, some losses para-aminophenol occur in each step.

In accordance with the present invention an improved method is provided for the recovery of para-aminophenol by flotation from crude solutions thereof, e.g. the aqueous acidic solution obtained by the catalytic hydrogenation of nitrobenzene.

The method of the present invention is particularly applicable to the crude para-aminophenol reaction product mixture obtained in the practice of the Benner U.S. Pat. No. 3,383,416 wherein an aqueous acidic reaction medium resulting from the catalytic hydrogenation of nitrobenzene, and after separation of any unreacted nitrobenzene, is employed as the starting material. The aqueous acidic layer contains, in addition to the para-aminophenol, certain impurities and by-products. Prior to contact with the aromatic amine, the acidic aqueous solution is neutralized with an alkali material such as ammonia. The pH of the crude para-aminophenol solution will then be raised to about 6.6 to 9, and preferably from about 7 to 7.4.

An important aspect of the present invention is the requirement of carrying out the neutralization at temperatures sufficiently low so that the para-aminophenol forms a fluffy precipitate. Temperatures below about 60° C., and preferably temperatures of about 40° C. or below are generally employed. It is of course possible to carry out the initial neutralization at higher temperatures until the pH is approximately 4, and then continuing the neutralization at relatively lower temperatures (e.g. 30° C.) so that the para-aminophenol precipitates as light fluffy crystals.

The next step in the method comprising adding to the neutralized mixture an aromatic amine such as aniline, ortho-toluidine, mixed toluidines, mixed xylidines, or mixtures thereof. It will be understood isomeric mixtures of xylidines and toluidines may be employed. By mixed toluidines is meant the mixture of isomers obtained by the reduction of mixed nitrotoluenes prepared by the nitration of toluene, and by mixed xylidines is meant the mixture of isomers obtained by the reduction of mixed nitroxylenes prepared by the nitration of xylenes. The amount of the aromatic amine employed will generally range from about 2 to 9 mols per mol of para-aminophenol present in the crude feed material, and preferably from about 3 to 4 mols per mol of para-aminophenol.

When the acidic solution is neutralized at temperatures below 60° C., and preferably below 40° C., the para-aminophenol precipitates in the form of fine crystals. After mixing the neutralized mass with an aromatic amine and allowing it to settle, three layers form. The upper layer contains most of the para-aminophenol suspended in the aromatic amine. The small intermediate layer is an amine-water emulsion which also contains small amounts of para-aminophenol. The clear lower layer is an aqueous solution of ammonium sulfate which contains negligible amounts of para-aminophenol. The aqueous layer is separated from the upper layers and is discarded or sold for its value as a fertilizer.

The upper layer of aromatic amine and the intermediate layer of water-amine emulsion contain substantially all of the para-aminophenol floating or suspended therein. These layers were found to be quite stable over a period of at least 3 days. When the combined layers were heated to a temperature of from about 75° to 90° C., preferably from about 75° to 80° C., two distinct layers form. The upper layer comprises a solution of para-aminophenol in the aromatic amine, whereas the lower layer is primarily an aqueous layer containing a minor proportion of the para-aminophenol. The presence of the para-aminophenol in the aqueous layer occurs because of the separation of the layers at elevated temperatures. This layer can be recycled to the crude feed prior to the neutralization step.

The aromatic amine layer contains substantially all of the para-aminophenol. It can be isolated by removal of the amine under reduced pressure. It is preferable, however, to utilize the solution of para-aminophenol in amine as such, for example, directly in the manufacture of other para-aminophenol derivatives, e.g. N,N'-diaryl-p-phenylenediamines.

As previously mentioned, the diaryl para-phenylenediamines have been used effectively as rubber antioxidants and antiozonants, sometimes referred to as antidegradants. Prior art pertaining to this field include U.S. Pat. Nos. 2,048,823 (Semon); 2,053,785 (Semon); 2,087,199 (Clifford); and 3,432,460 (Spacht). The principal commercial method involves the reaction of hydroquinone with an aromatic amine or aromatic amine mixture in the presence of a condensation catalyst as described in U.S. Pat. No. 3,432,460. The hydroquinone reactant has however become quite expensive, and its cost has led to a substantial increase in the prices of the diaryl para-phenylenediamines.

Other methods have been proposed for the preparation of the diaryl para-phenylenediamines. For example, in U.S. Pat. No. 3,432,460 the hydroquinone is replaced by para-aminophenol, and the reaction with the aromatic amine is in relatively large excess is carried out in the presence of alkylation catalyst such as iodine, matallic halides, phosphoric acid, alkyl phosphates, aniline halides, ammonium halides, etc. The disclosure of this U.S. patent are incorporated herein by reference with respect to the preparation of diaryl para-phenylenediamines as well as to the rubbers whose antidegradant properties can be enhanced by the incorporation of diaryl para-phenylenediamines.

In accordance with one aspect of the present invention, a method has been discovered whereby diaryl-phenylenediamines can be prepared economically from para-aminophenol that has been extracted from crude solutions thereof, e.g. the aqueous acidic solution obtained by the catalytic hydrogenation of nitrobenzene. It was further found that the impurities normally associated with such crude para-aminophenol will not interfere deleteriously in the conversion of the para-aminophenol by reaction with aromatic amines to form the desired diaryl para-phenylenediamine products. In addition it was discovered that the para-aminophenol could be effectively recovered from its crude solution by flotation or suspension in aromatic amines such as, for example, aniline, mixed toluidienes, ortho-toluidine, mixed xylidines, and mixtures of these amines.

The aromatic amine extract will contain the para-aminophenol and may contain minor amounts of impurities or byproducts such as aniline, p-aminodiphenylamine, p-hydroxydiphenylamine, and 4,4' diaminodiphenylether. Oxidation and reduction derivatives of the foregoing may also be present. Another advantage resulting from the recovery of para-aminophenol according to the present invention is that impurities such as p-aminodiphenylamine and p-hydroxydiphenylamine also form the desired diaryl para-diphenylenediamines by further reaction with the aromatic amine.

This aromatic amine extract, after the above described heat treatment may be sent either directly to storage or to a reactor wherein it is contacted with an alkylation or condensation catalyst at a temperature of from about 100° to 325° C., preferably from about 185° to 250° C., and at pressures ranging from atmospheric to 100 psig. As is usual for this reaction, the apparatus is designed to effect the continuous removal of water as it is formed from the reaction product mixture. The alkylation or condensation catalyst is selected from the group consisting of iodine, ferric chloride, ferric hydroxide, sulfanilic acid, copper sulfate, copper chromite, phosphoric acid, alkyl phosphates, alkylphosphites, aniline halides, ammonium halides, etc. Only catalytically effective amounts of such condensation catalysts need be employed.

The alkylation or condensation reaction may be carried by either one-or two-steps conversion processes. In either process the reaction proceeds by the initial formation para-hydroxydiphenylamine which is then coverted to the diaryl para-phenylenediamines. For certain procedures the first step may be carried out with sulfanilic acid as the catalyst, while ferric chloride is used in the second step. In other procedures, these catalysts have been used alone or in an admixture.

The resulting diaryl para-phenylenediamine products may be recovered from the reaction product mixture by vacuum distillation, preferably after destroying the catalyst.

As previously mentioned, the process of the present invention may be carried out in a continuous or batchwise manner involving the sequential steps discussed in detail above. In contrast to the known process wherein solid or separated para-aminophenol is fed to the reaction zone along with the aromatic amine reactant, the present process involves the use of a liquid feed solution which contains not only the para-aminophenol but the aromatic as well. The latter material functions in two separate and distinct manners. Firstly, the aromatic amine is used to extract the para-aminophenol from a crude aqueous acidic solution thereof. Secondly, the aromatic amine reacts with the para-aminophenol in a subsequent step without any intermediate separation in the presence of a condensation catalyst to form the desired diaryl para-phenylenediamines.

Typical diaryl para-phenylenediamines which can be produced in accordance with the process of the present invention included, but are not limited to, the following compounds and mixtures thereof:

N,N'-diphenyl-para-phenylenediamine
N,N'-ditolyl-para-phenylenediamine
N,N'-dixylyl-para-phenylenediamine
N-phenyl, N-tolyl-para-phenylenediamine
N-phenyl, N-xylyl-para-phenylenediamine
N-tolyl, N-xylyl-para-phenylenediamine, etc.

This invention is illustrated in greater detail by the example given below although it is not intended in any way to limit the invention thereto.

EXAMPLE I

A solution which simulates the reaction mass obtained in the U.S. Pat. No. 3,383,416 by reduction of nitrobenzene after removal of catalyst and unreacted nitrobenzene was prepared from 5.0 g. para-aminophenol (m.p 185°–186° C.), 1.3 g. aniline, 6.5 g. sulfuric acid, and 50 g. water. The solution was neutralized with anhydrous ammonia to a pH of 7.0 to 7.2, then allowed to cool to room temperature. Aniline (17 g., approximately 4 mol/mol PAP) was added and mixed in thoroughly. The precipitated para-aminophenol became suspended in the aniline. The mixture was allowed to stand undisturbed and the aniline separated as an upper layer with a partial emulsion forming at the amine-water interface, carrying with it the suspended para-aminophenol. The lower clear ammonium sulfate solution (40 g.) was removed and discarded. The remainder of the mixture was heated to 85° C. to give two distinct layers which were separated. Precipitates formed in both samples when they were allowed to cool to room temperature (23° C.). The precipitate that formed in the aqueous sample was extracted readily at room temperature with 10 g. of aniline, then the aqueous sample was discarded. The two aniline extracts were combined and the aniline was removed under reduced pressure to give 4.8 g. (96% recovery) of the para-aminophenol (m.p. 184°–186° C.).

EXAMPLE II

A 251.6 g. sample (estimated to contain 20 g. to 23 g. by weight) of the crude para-aminophenol reaction product obtained by the practice of the process of U.S. Pat. No. 3,383,416 stripped of nitrobenzene but prior to neutralization was neutralized with anhydrous ammonia to a pH of 7.0 to 7.2, and allowed to cool to 30° C. Aniline (68.6 g. approximately 4 mols/mols of PAP) was added to the neutralized sample and mixed thoroughly. The precipitated para-aminophenol became suspended in the aniline phase. When the mixture was allowed to stand undisturbed, the aniline phase gradually separated and formed an upper layer with a partial emulsion in the aqueous layer immediately below it. The precipitates p-aminophenol remained suspended in the aniline. The lower clear ammonium sulfate solution (164 g, approx. 76% of total) was separated and discarded. The remainder of the mixture was heated to 75°–80° C. to give two distinct layers which were separated. The aqueous layer (51 g., approx. 24% of total) was discarded. However, if sequential experiments were to be performed, it could be added to the next reaction sample to be processed. Aniline was removed from the amine phase under reduced pressure, and the solid collected was washed twice with 5 g. portions of ice water, then dried. The yield of crude p-aminophenol was 23.6 g. (m.p. 175°–180° C.).

EXAMPLE III

Crude para-aminophenol recovered by extraction from a 251.6 g. sample of its reduction as used in Example II was combined with a total of 124 g. of aniline and 3 g. of ferric chloride hexahydrate in a reaction vessel. The mixture was heated at 180°–200° C. for 18 hours during which time water from the catalyst and ammonia from the reaction were distilled from the reaction mass. The reaction temperature was then increased to 250°–260° C. (some aniline and water from the reaction were removed during this process) and maintained at that temperature for 5 hours. The reaction mixture was allowed to cool to 110° C., and 5.4 g. of a 25% aqueous sodium hydroxide solution were added to destroy the catalyst. After dilution of the mixture with 50 g. of aniline, the water present was removed by distillation and the hot residue was filtered to remove the iron salts. The filtrate was concentrated under reduced pressure and vacuum distilled to give 30 g. of N,N'-diphenyl-p-phenylenediamine (DPPD), b.p. 200°–230° C. (0.3 mm Hg), m.p. 133°–137° C. The forecuts boiling below 200° C. (0.3 mm Hg) contained considerable unreacted para-hydroxydiphenylamine and the distillation residue also contained N,N'-diphenyl-p-phenylenediamine.

EXAMPLE IV

A solution which simulates the reaction mass obtained in the U.S. Pat. No. 3,383,416 by reduction of nitrobenzene after removal of catalyst and unreacted nitrobenzene was prepared from 5.0 g. para-aminophenol (m. p. 182°–186° C.), 1.3 g. aniline, 6.5 g. sulfuric acid, and 50 g. water. The solution was neutralized with anhydrous ammonia to a pH of 7.0 to 7.2, then allowed to cool to room temperature. A sample of mixed toluidines (DuPont) (19.6 g, 0.183 mol, approx. 4 mols/mol PAP) was added and admixed thoroughly. The precipitated para-aminophenol became suspended in the mixed toluidines. The mixture was allowed to stand undisturbed and the toluidines separated as an upper layer with a partial emulsion forming at the amine-water interface, carrying with it the suspended para-aminophenol. The lower clear ammonium sulfate solution (51 g.) was removed and discarded. The remainder of the mixture was heated to 90°–95° C. to give two distinct layers which were separated. Precipitates formed in both samples when they were allowed to cool to room temperature (23° C.). The precipitate that formed in the aqueous sample was extracted at room temperature with 10 g. of the mixed toluidines, then the aqueous sample was discarded. The two toluidine extracts were combined and the toluidines were removed under reduced pressure to give 4.9 g. (98% recovery) of the para-aminophenol (m. p. 182°–186° C.).

EXAMPLE V

The procedure described above in Example IV was performed with a sample of mixed xylidines (DuPont) (22.1 g., 0.183 mol, approx. 4 mols/mol PAP) instead of the mixed toluidines.

After the xylidines had been mixed with the neutralized sample and the layers had separated, the lower clear ammonium sulfate solution (55 g.) was removed and discarded. The remainder of the mixture was heated to 90°–95° C. to give two distinct layers which were separated. Precipitates formed in both samples when they were allowed to cool to room temperature. The precipitate that formed in the aqueous sample was extracted with 10 g. of the mixed xylidines, and the aqueous sample was discarded. The two xylidine extracts were combined and the xylidines were removed under reduced pressure to give 4.3 g. (86% recovery) of the para-aminophenol (m. p. 182°–186° C.).

The above examples and data demonstrate that the improved method of this invention has the advantage of providing a relatively low cost solution of para-aminophenol in an aromatic amine which, for example, can be reacted directly in the presence of an alkylation or condensation catalyst to produce the desired diaryl para-phenylenediamines. Not only are expensive intermediate separation and purification steps eliminated, but it has been further shown that the impurities present in the crude para-aminophenol starting material do not adversely affect the reaction between the para-aminophenol and the aromatic amine. Moreover, the impurities do not impair the usefulness of the diaryl para-phenylenediamine products.

It will be understood that, although crude para-aminophenol solution utilized in the process of this invention is preferably derived by the reduction of nitrobenzene with hydrogen in an acid solution, e.g. sulfuric acid solution as described in the Benner Patent; crude para-aminophenol derived from other processes may be utilized by introducing such material into an aqueous acidic solution and then carrying out the process as set forth above. The acidic solution can be a mineral acid such as sulfuric acid or hydrocholoric acid and the like or a low molecular weight organic acid such as acetic acid and the like. In an alternative embodiment crude p-aminophenol wet cake or a crude dry p-aminophenol is admixed with aromatic amine and water. When carrying out this latter procedure no adjustment in pH is made during the treatment.

While particular embodiments of this invention are shown above it will be understood that the invention is obviously subject to variations and modifications without departing from its broader aspects. Thus, the step of extracting the para-aminophenol from crude solutions thereof by utilizing aromatic amines may be utilized in a process directed primarily to the purification of para-aminophenol or in a process of converting the para-aminophenol to derivatives other than diaryl para-phenylenediamines.

What is claimed is:

1. An improved method for the recovery of para-aminophenol from an aqueous acidic solution thereof obtained by the catalytic hydrogenation of nitrobenzene which comprises neutralizing the crude acidic solution at a temperature sufficiently low whereby the para-aminophenol precipitates as a fluffy precipitate, admixing an aromatic amine with the neutralized solution to form an upper layer comprising the para-aminophenol precipitate suspended in the aromatic amine and a lower aqueous layer, and then separating the upper layer from the lower layer.

2. The method of claim 1 wherein the aromatic amine is aniline.

3. A method for the recovery of para-aminophenol in an aromatic amine solution from a crude aqueous solution containing para-aminophenol which comprises the following sequential steps:
   (a) adjusting the pH of the crude aqueous solution to about 6.6 to 9 at a temperature below about 30° C. whereby said para-aminophenol precipitates as crystals;
   (b) contacting the thus treated crude aqueous solution with an aromatic amine in a mol ratio of from about 2 to 9 mols of the aromatic amine per mol of para-aminophenol to form an upper layer comprising said aromatic amine and said crystallized para-aminophenol and a lower aqueous layer;
   (c) separating the upper layer from the lower layer;
   (d) heating the separated upper layer to a temperature within the range of about 75° to 90° C., to form a second upper layer comprising a solution of the aromatic amine and the para-aminophenol and a second lower aqueous layer; and
   (e) separating said second upper layer solution formed in step (d) from the second lower aqueous layer.

4. The method of claim 3 wherein the aromatic amine is aniline.

5. The method of claim 3 wherein the aromatic amine is mixed xylidines.

6. The method of claim 3 wherein the aromatic amine is mixed toluidines.

7. The method of claim 3 wherein the pH of the crude aqueous acidic solution is adjusted initially at from below about 2 to a pH of about 4 and then to a pH of from 7 to 7.4 at a temperature of below about 40° C.

8. The method of claim 3 wherein the crude aqueous acidic solution is stirred in step (b) while being contacted with the aromatic amine.

9. A method for the preparation of diaryl para-phenylenediamines from a crude aqueous sulfuric acid solution containing para-aminophenol, said crude aqueous solution being obtained by the catalytic hydrogenation of nitrobenzene in aqueous sulfuric acid, which comprises the following sequential steps:
   (a) adjusting the pH of the crude aqueous solution to about 6.6 to 9 whereby said para-aminophenol precipitates as crystals;
   (b) contacting the thus treated crude aqueous solution by contacting it with an aromatic amine selected from the group consisting of aniline, mixed toluidines, mixed xylidines, ortho-toluidine, and mixtures thereof, the amount of aromatic amine ranging from about 2 to 9 mols per mol of para-aminophenol to form an upper layer comprising the aromatic amine and said crystallized para-aminophenol and a lower aqueous layer comprising sulfate formed by the neutralization of the sulfuric acid;
   (c) separating the upper layer from the lower layer;
   (d) heating the separated upper layer to a temperature within the range of about 75° to 90° C. to form a second upper layer comprising a solution of the aromatic amine and the para-aminophenol and a second lower aqueous layer;
   (e) separating said second upper layer solution containing the aromatic amine and the para-aminophenol from the second lower aqueous layer;
   (f) passing said separated second solution to a reaction zone where it contacts a condensation catalyst at a temperature of from about 105° to 250° C. whereby the para-aminophenol and the aromatic amine react and form corresponding diaryl para-phenylenediamines; and
   (g) recovering the diaryl para-phenylenediamines from the resulting reaction product mixture.

10. The method of claim 9 wherein the aromatic amine is aniline.

11. The method of claim 9 wherein the aromatic amine is mixed xylidines.

12. The method of claim 9 wherein the aromatic amine is mixed toluidines.

* * * * *